United States Patent [19]
Blincko

[11] Patent Number: 5,256,409
[45] Date of Patent: Oct. 26, 1993

[54] IMMUNOGENIC COMPOSITION AGAINST TRICYCLIC ANTIDEPRESSANT DRUGS

[75] Inventor: Stuart J. F. E. Blincko, Sussex, United Kingdom

[73] Assignee: Therapeutic Antibodies, Inc., Nashville, Tenn.

[21] Appl. No.: 645,799

[22] Filed: Jan. 25, 1991

[30] Foreign Application Priority Data

Jan. 25, 1990 [GB] United Kingdom ............... 9001694

[51] Int. Cl.$^5$ ................ A61K 39/395; A61K 39/385; C07K 17/06
[52] U.S. Cl. .................... 424/85.8; 424/88; 424/89; 424/90; 424/91; 424/92; 424/94.3; 530/363; 530/405; 530/409; 530/395; 530/807; 436/546; 525/54.1
[58] Field of Search ............... 530/363, 405, 409, 807, 530/395; 525/54.1; 424/85.8, 88, 89, 92, 90, 91, 94.3; 436/546

[56] References Cited

U.S. PATENT DOCUMENTS

| | | | |
|---|---|---|---|
| 4,235,864 | 11/1980 | Kaul et al. | 530/363 |
| 4,495,281 | 1/1985 | Buckler et al. | 435/7 |
| 4,620,977 | 11/1986 | Strahilevitz | 424/88 |
| 4,629,691 | 12/1986 | Collins et al. | 435/7 |
| 4,780,312 | 10/1988 | Talwar | 424/88 |

OTHER PUBLICATIONS

O'Callaghan et al., (1987) J. Neurochemistry 49 C4):109/-5.
Chu et al. (1982) J. Immunol. Methods 55:73-78.
Erlanger (1980) Methods Enzymol. 70:85-104.
Liu et al., (1987) Clin. toxicol. 25(7):527-538.
Dart et al. (1991) Vet. Hum. Toxicol. 33(4) Abstr. #31.
Brunn et al., (1991) Int. J. Immunopharmac. 13(7) 841-851.
K. P. Maguire et al., "A Radioimmunoassay For Nortriptyline (And Other Tricyclic Antidepressants) In Plasma", Clinical Chemistry, 24(4): 549-554 (1978).
G. W. Aherne, et al., "The Radioimmunoassay of Tricyclic Antidepressants", British Journal of Clinical Pharmacology, 3:561-565 (1976).
G. P. Mould et al., "Radioimmunoassay of Amitriptyline and Nortriptyline In Body Fluids", Annals of Clinical Biochemistry, 15:221-225 (1978).
G. W. Aherne et al., "Radioimmunoassay For Nortriptyline and Amitriptyliner", The Lancet, p. 1214 (Jun. 4, 1977).
J. D. Robinson, et al., "Measurement of Plasma Nortriptyline Concentrations: Radioimmunoassay and Gas-Chromatography Compared", Clinical Chemistry, 24(11):2023-2025 (1978).
J. D. Robinson et al., "A Radioimmunoassay For The Determination of Combined Amitriptyline and Nortriptyline Concentrations In Microliter Samples of Plasma", The Journal of Pharmacology and Experimental Therapeutics, 205(2):499-502 (1978).
K. Robinson et al., "Radioimmunoassay of Tricyclic Antidepressant and Some Phenothiazine Drugs In Forensic Toxicology", Journal of Immunoassay, 6(1&2):11-22 (1985).
S. Spector et al., "Radioimmunoassay For Desmethylimipramine", Psycho-Pharmacology Communications, 1(4):421-429 (1975).
B. Kaul et al., "Screening For Tricyclic Antidepressant Drugs In Biological Specimens By Radioimmunoassay", Journal of Analytical Toxicology, 1:236-243 (Sept./Oct. 1977).

(List continued on next page.)

Primary Examiner—Christine M. Nucker
Assistant Examiner—Kay K. Kim
Attorney, Agent, or Firm—Finnegan, Henderson, Farabow, Garrett & Dunner

[57] ABSTRACT

An immunogenic composition for raising antisera to a drug comprising immunologically active carrier protein to which is bound at least two types of hapten, each hapten comprising a drug molecule and, optionally, a bridging group, a method of raising antisera to a drug using said immunogenic composition, and a method of alleviating an overdose of a tricyclic depressant drug comprising an effective amount of antisera raised to an immunogen.

18 Claims, 2 Drawing Sheets

OTHER PUBLICATIONS

R. Lucek et al., "Specific Radioimmunoassay For Amitriptyline and Nortriptyline In Plasma", Research Communications in Chemical Pathology and Pharmacology, 18(1):125–136 (Sep. 1977).

J. W. Hubbard et al., "Radioimmunoassay For Psychotropic Drugs II: Synthesis and Properties Of Haptens For Tricyclic Antidepressants", Journal of Pharmaceutical Sciences, 67(11):1571–1578 (Nov. 1978).

K. K. Midha et al., "Monitoring Of Therapeutic Concentrations of Psychotropic Drugs In Plasma By Radioimmunoassays", Journal of Analytical Toxicology, 2:185–192 (Sep./Oct. 1978).

G. F. Read et al., "A Specific Radio-immunoassay Procedure For Plasma Clomipramine", Postgraduate Medical Journal, 53(4):110–116 (1977).

G. F. Read et al., "Determination of A Tricyclic Antidepressant, Clomipramine (Anafranil), In Plasma By A Specific Radioimmunoassay, Procedure", Clinical Chemistry, 24(1):36–40 (1978).

D. J. Brunswick et al., "Radioimmunoassay of Imipramine and Desmethyl-imipramine", Life Sciences, 22(2):137–146 (1978).

D. J. Brunswick et al., "Specific Radioimmunoassay of Amitriptyline And Nortriptyline", British Journal of Clinical Pharmacology, 7:343–348 (1979).

P. A. Mason et al., "Development and Evaluation Of A Radioimmunoassay For The Analysis Of Body Fluids To Determine The Presence Of Tricyclic Anti-depressant Drugs", Analyst. 109:1213–1215 (Sep. 1984).

R. S. Kamel et al., "Novel 125I-Labeled Nortriptyline Derivatives And Their Use In Liquid-Phase Or Magnetizable Solid-Phase Second-Antibody Radioimmunoassays", Clinical Chemistry, 25(12):1997–2002 (1979).

R. Virtanen, "Radioimmunoassay For Tricyclic Antidepressants", The Scandinavian Journal of Clinical & Laboratory Investigation, 40:191–197 (1980).

H. Denis et al., "Enzyme-Linked Immunosorbent Assay For Amitriptyline and Other Antidepressants Using A Monoclonal Antibody", Clinica Chimica Acta, 159:257–267 (1986).

M. N. Al-Bassam et al., "Double-Antibody Enzyme Immunoassay For Nortriptyline", Clinical Chemistry, 24(9):1590–1594 (1978).

R. C. Dorey, "Results Compared For Tricyclic Antidepressants As Assayed By Liquid Chromatography And Enzyme Immunoassay", Clinical Chemistry, 34(11):2348–2351 (1988).

B. A. Scoggins et al., "Measurement of Tricyclic Antidepressants, Part I, A Review of Methodology", Clinical Chemistry, 26(1):5–17 (1980).

B. A. Scoggins et al., "Measurement Of Tricyclic Antidepressants, Part II, Applications Of Methodology", Clinical Chemistry, 26(7):805–815 (1980).

P. Pentel et al., "Redistribution Into Plasma Of Tracer Doses Of Desipramine by Anti-desipramine Antiserum In Rats", Biochemical Pharmacology, 36(2):293–295 (1987).

A. Sabouraud et al., "The Effect Of Nortriptyline-specific Active Immunization On Amitriptyline Toxicity And Disposition In The Rabbit", Toxicology, 62:349–360 (1990).

M. J. Hursting et al., "Tricyclic Antidepressant-Specific Fab Fragments Alter The Distribution and Elimination Of Desipramine In The Rabbit: A Model For Overdose Treatment", Clinical Toxicology, 27(1&2):53–66 (1989).

P. R. Pentel et al., "Redistribution Of Tricyclic Antidepressants In Rats Using A Drug-Specific Monoclonal Antibody: Dose-Response Relationship", Drug Metabolism and Disposition, 19(1)24–28 (1991).

P. R. Pental et al., "Pretreatment With Drug-Specific Antibody Reduces Desipramine Cardiotoxicity In Rats", Life Sciences, 48(7):675–683 (1991).

A. Sabouraud et al., "Immunotherapy Of Tricyclic Antidepressant Poisoning: Recent Experimental Data", Lyons Poison Center's 30th Anniversary and EAPCCT Technical Meeting (May 22–24, 1991).

A. J. Heath, "Immunotherapy For Tricyclic Antidepressant Poisoning: A Clinical Perspective", Lyons Poison Center's 30th Anniversary and EAPCCT Technical Meeting (May 22–24, 1991).

IMMUNOGENIC COMPOSITION AGAINST TRICYCLIC ANTIDEPRESSANT DRUGS

BACKGROUND OF THE INVENTION

1. Field of Invention

The present invention relates to immunogenic compositions and to methods for raising antisera to small molecules.

2. Description of Related Art

Antisera are raised by immunising an animal with an immunogen. In general, antisera to a small molecules, such as drugs, cannot be raised using an immunogen comprising the small molecule alone. It has been shown, however, that antisera to drugs may be raised by linking the drug to a large "carrier protein" and immunising animals, for example sheep or rabbits, with the drug-protein conjugate. Reaction Scheme 1 outlines the steps involved in raising antibodies to the drug (F=functional group able to covalently link to protein. The immunogen is prepared by covalently bonding suitably derivatised drug molecules to the carrier protein by means by a bridging group. Antisera are raised in and isolated from animals immunized with the immunogen.

REACTION SCHEME 1

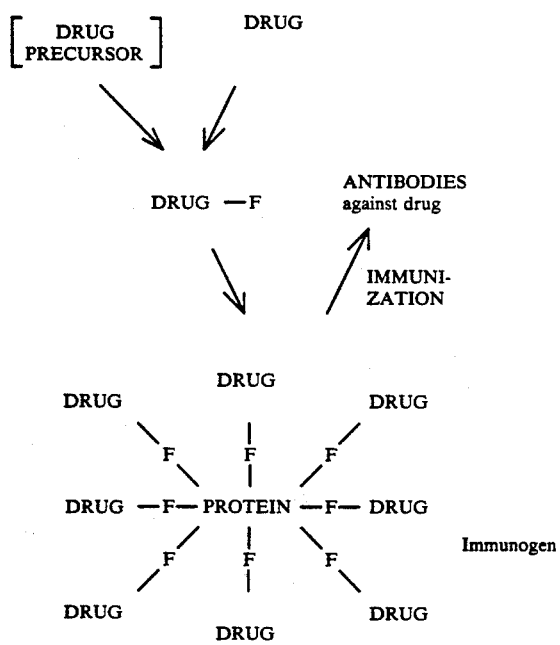

For example, immunogens have been reported for use in raising polyclonal antisera to tricyclic antidepressants (TCA) drugs for use in radioimmunoassays.

Tricyclic antidepressant drugs are a closely related series of compounds with a three ring molecular core. Examples include Desipramine (I) and Nortriptyline (II) (shown below).

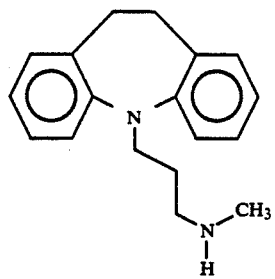

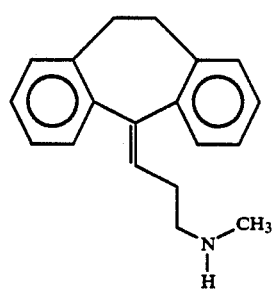

Brunswick et al., *Life Science* (1978) 22: 137-146, have prepared the following immunogen:

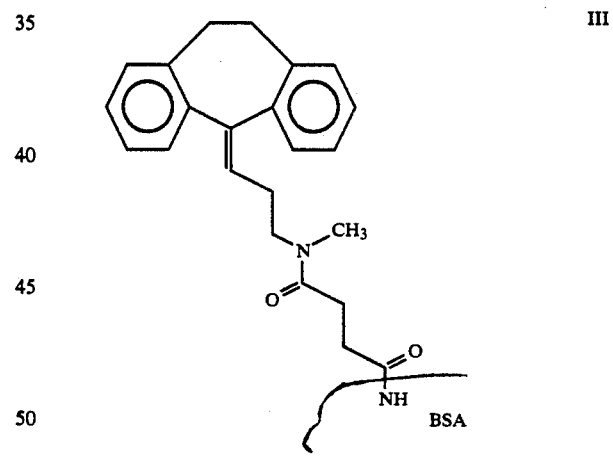

This immunogen comprises the TCA drug Nortriptyline bonded, via the tail portion of the molecule, to BSA (Bovine serum albumin), as the carrier protein, by means of a hemisuccinate bridge. The immunogen was used to immunise rabbits.

Read et al., [Post Grad. Med. J. (1977) 53: Suppl. 4: 110-116], have shown that the antisera to TCA drugs may also be raised by immunogens in which the drug is linked to the carrier protein by means of a bridging group bonded to the ring system of the drug:

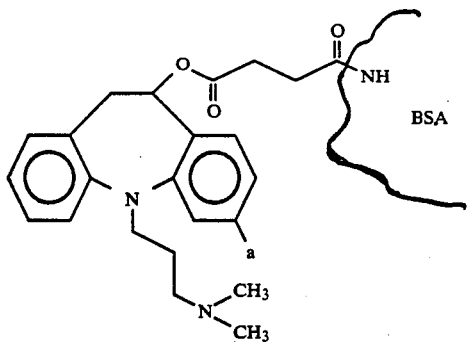

TCA drugs are widely used for the treatment of major depression. In excessive amounts, however, they cause a number of toxic effects, especially on the heart and, because of the type of patient to whom they are given, are one of the most common drugs taken in suicide attempts. In the USA they account for about 300 drug deaths (accidental and suicide) of a total of 4,000 drug deaths (accidental and suicide) per year.

To be useful in the treatment of a TCA drug overdose the antibodies contained in the antisera must bind the TCA drug thereby reducing the concentration of the free drug in the body. It is calculated, based on an approximate molecular weight of 280 for a TCA drug and an approximate molecular weight of 150,000 for an antibody (whole IgG) that 540 g of antibody would be required to bind 1 g of drug. If, however, just the Fab fragment of the antibody is used in therapy approximately 180 g of Fab would be required to bind 1 g of drug (assuming an approximate molecular weight of 50,000 for a Fab fragment).

The estimation of the amount of TCA drug to be bound by specific Fab in the treatment of an overdose is not simple. The drugs have highly variable volumes of distribution (10–50 l/kg) and, it has been suggested that, neither toxicity nor therapy correlates well with blood concentration [Cantrill et al., J. Emerg. Med. (1983) 1:169–177; and Ware et al., Southern Med. J. (1987) 80:1410–15].

Table I lists the properties of the TCA drugs:

TABLE I

| TCA DATA | Average | Range |
| --- | --- | --- |
| Normal Dose | 150 mg | 25–300 mg |
| Potentially lethal dose | 1500 mg | 500–10,000 mg |
| Potentially lethal dose per kg | 20 mg/kg | 20–40 mg/kg |
| Therapeutic circulating level | 0.15 mg/l | 0.05–0.3 mg/l |
| Toxic blood concentration | 1.0 mg/l | much variation |
| Blood concentration (pm cases) | 10.0 mg/l | 0.47–35 mg/l |
| Tissue concentration (pm cases) | | 6–26 mg/l |
| Half life | Desipramine 18 h Nortriptyline 31 h | |
| Volume of distribution | 30 l/kg | 10–50 l/kg |

Using the above figures, it is estimated that between 300 g and 4000 g of specific Fab would be required to neutralise all the drug in an overdose. This may be too large a dose for administration to a patient. If it were found that all the drug in an overdose had to be neutralized to save the patient then this therapy might not be feasible. However, very little of the drug circulates free in the blood where it can cause the most damage (to the heart). It is suggested therefore that a much lower dose of Fab, of the order of 8 g, may be required to save the patient's life.

8 g is a quantity that can reasonably be administered to a patient. Thus, treatment of an overdose requiring binding of the TCA drug in the blood and to reverse the toxic effect on the hear of the patient is a practically feasible proposition.

For production of antisera to TCA drugs to be economically viable however, it is desirable that the titre of the specific antisera raised in, for example, sheep, should exceed 4 g/l.

In addition, it is desirable that the antisera produced bind well to a broad spectrum of TCA drugs.

Known immunogens suffer, however, from a number of drawbacks including first, that animals immunized with these immunogens produce only a low titre of antisera specific to the drugs; and secondly, the antisera produced is of low cross-reactivity, i.e. the antisera exhibits poor reactivity against a series of drug molecules containing small structural variations.

There remains, therefore, a need for immunogenic compositions capable of raising a high titre antisera. There also remains a need for immunogenic compositions capable of raising antisera showing high cross-reactivity with a series of related drugs.

SUMMARY OF THE INVENTION

According to the first aspect of the present invention there is provided an immunogenic composition for raising antisera to a drug comprising immunologically active carrier protein to which is bound at least two types of hapten, each hapten comprising a drug molecule and, optionally, a bridging group.

According to a second aspect of the present invention there is provided a method of raising antisera to a drug wherein an immunogenic composition according to the first aspect of the present invention is used to immunise an animal.

According to the third aspect of the present invention there is provided a process for the preparation of a pharmaceutical composition comprising mixing antisera raised to an immunogen according to the first aspect of the present invention with a pharmaceutically acceptable excipient.

According to the fourth aspect of the present invention there is provided a method of alleviating an overdose of a tricyclic antidepressant drug comprising administering to a patient suffering from such an overdose an effective amount of antisera raised to an immunogen according to the first aspect of the present invention.

BRIEF DESCRIPTION OF THE DRAWINGS

The invention is described with reference to the Figures in which.

DESCRIPTION OF THE PREFERRED EMBODIMENTS

Figure 1:
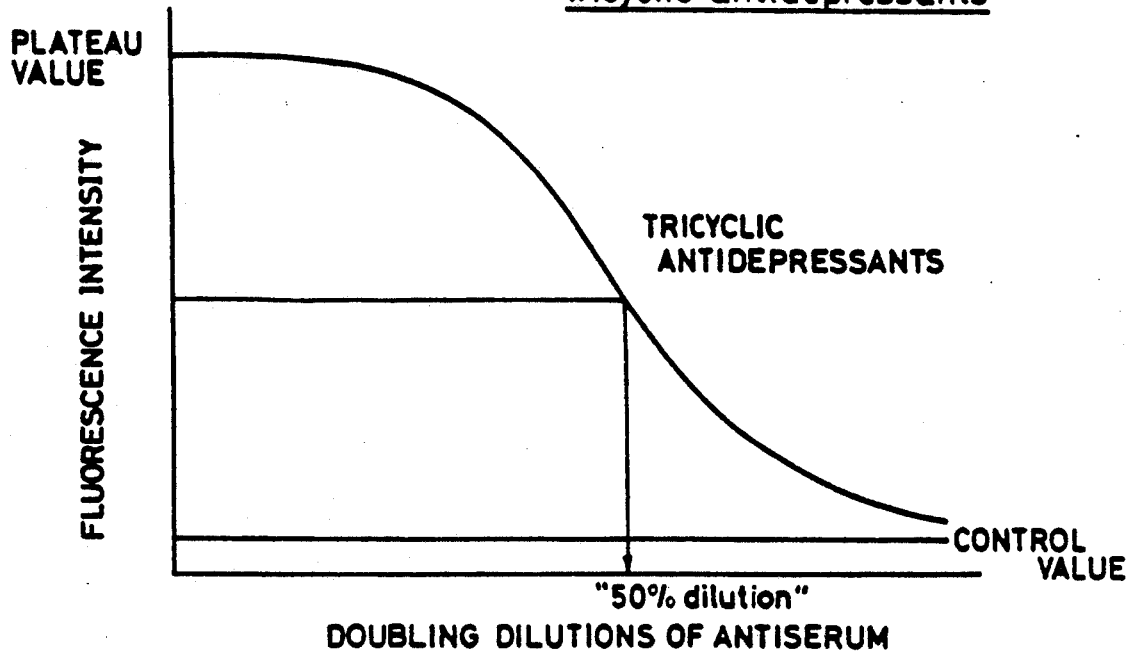
FIG. 1 illustrates a typical dilution curve obtained in an enhancement fluoroimmunoassay by plotting fluorescence against the dilution of antisera.

It has been found that immunogenic compositions containing more than one type of hapten are particularly effective in raising antisera of advantageously high titre and/or cross-reactivity.

Preferably, in use the immunogen raises high titre antisera to a drug. Preferably, in use the immunogen raises antisera to a drug of a titre greater than 4.0 g/l, more preferably, greater than 5.0 g/l.

Preferably, the immunogenic composition comprises an immunogen comprising an immunologically active carrier protein to which is bound at least two types of hapten.

Thus, each carrier protein molecule has bound to it at least two different types of hapten.

Alternatively, the immunogenic composition comprises a mixture of at least two types of immunogens, each immunogen comprising an immunologically active carrier protein to which is bound at least one type of hapten.

Preferably, the different types of hapten differ in the drug molecules.

Alternatively, the different types of hapten differ in the bridging group.

Alternatively, the different types of hapten differ in both the drug molecule and the bridging group.

The scope of the invention may be illustrated diagrammatically as including immunogenic compositions.

1. Immunogens comprising one drug compound bound to the carrier protein by two or more bridging groups.

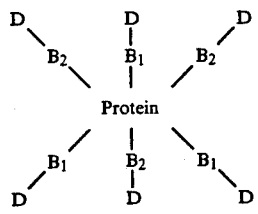

2. Immunogens comprising two or more drug compounds bound to the carrier protein by one bridging group.

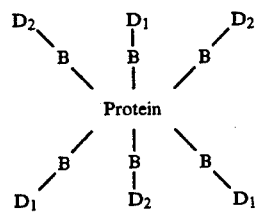

3. Immunogens comprising two or more drug compounds bound to the carrier protein by two or more bridging groups.

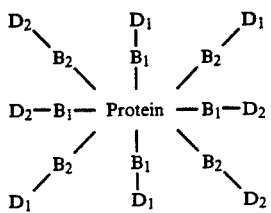

4. Immunogenic compositions comprising two or more immunogens differing in the drug compounds.

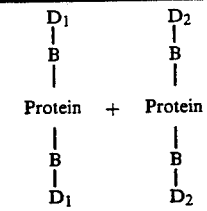

5. Immunogenic compositions comprising two or more immunogens differing in the bridging groups.

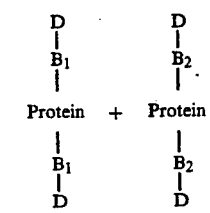

6. Immunogenic compositions comprising two or more immunogens different in both the drug compounds and bridging groups.

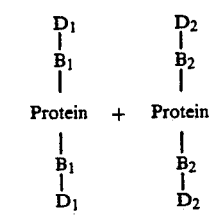

It will be appreciated that more complex variants of the above examples are included within the scope of the invention.

Optionally, one or more of the haptens do not comprise a bridging group such that the drug is bound directly to the carrier protein.

Preferably, each drug molecule is bound to the carrier protein by means of a bridging group.

The bridging group may be of any number of atoms in length and of any suitable chemical composition. It may be hydrophobic or hydrophillic in character (or a combination of both), polar or non-polar (or a combination of both), organic or inorganic (or a combination of both).

Advantageously, the bridging group is a non-polar and/or hydrophobic. It has been found that the bridge design plays a vital role in the quality of antisera produced.

The bridging group, if organic, may be aliphatic or aromatic, saturated or unsaturated (or combinations thereof) in character. The bridging group may be an amino acid, peptide or protein (synthetic or natural) or derivatives of these. The bridging group may be a saccharide, polysaccharide or carbohydrate (synthetic or natural) or derivatives of these. The bridging group may be polymeric such as a poly amino acid or other synthetic polymer.

Preferably, the bridging group is conformationally rigid or semi-rigid such that the orientation of the drug with respect to the carrier protein may be controlled. By "conformationally rigid or semi-rigid" is meant of limited intra-group rotational and translational degrees of freedom. Examples of such rigid or semi-rigid bridging groups include cyclic groups such as cyclohexyl, steroidal and carbohydrate groups or derivatives thereof.

The bridging group may be linked to the carrier protein and to the drug molecule by means of a wide variety of functional groups including:

—CO$_2$H

—SH
—NH₂
-maleimide
-isothiocyanate
-isocyanate
-active esters e.g. —CONHS, NHS=N-hydroxysuccinimide
—COX where X=halogen or other leaving group e.g. N₃⁻
-aryl azide—with UV activation
-phenylN₂⁺X⁻ X=halogen or other counter ion
—CH₂-Tosyl
—CH₂-Tresyl
—CH₂—X X=halogen or other leaving group e.g. OSO₂CH₂CF₃
—SO₃H
—SO₂Cl
—S—S—P where P may be pyridine or any other group e.g. cystine
—CO—O—CO—R anhydride or mixed anhydride
Traut's reagent
cyanuric chloride and derivatives thereof
-chloroformates and other formates e.g. —O—CO—imidazole
vinyl sulphones The carrier protein may comprise any peptide or protein capable of inducing an immunogenic response when used to immunise an animal. The protein or peptide may be synthetic or natural. Preferably, the carrier protein comprises keyhole limpet haemacyanin (KLH), bovine serum albumin (BSA), human serum albumin (HSA), polytufsin or other repeating unit polypeptides, polyamino acids or random copolymers of amino acids, or lysozyme or other enzymes. More preferably, the carrier protein comprises keyhole limpet haemacyanin. It has been found that immunogens in which the carrier protein comprises keyhole limpet haemacyanin are particularly effective at raising high titre antisera.

The drug may comprise any organic or inorganic molecule, natural or synthetic.

Preferably, where an immunogenic composition of the present invention comprises more than one drug compound, the drug compounds are structurally related.

Preferably, the drug comprises a tricyclic antidepressant drug (TCA drug).

Examples of TCA drugs include: Amitriptyline, Butriptyline, Clomipramine, Desipramine, Dibenzepine, Dothiepin, Doxepin, Imipramine, Iprindole, Maprotiline, Mianserin, Nomifensine, Nortriptyline, Opipramol, Protriptyline, Trimipramine, Zimelidine; and compounds structurally related thereto.

Preferably, the immunogenic composition comprises an immunogen comprising an immunologically active carrier protein to which is bound, optionally by means of bridging groups, two different TCA drug compounds.

Preferably, the two different TCA drug compounds comprise one drug compound of the desipramine/imipramine class of TCA drugs (represented by formula A) and one drug compound of the nortriptyline/amitriptyline class of TCA drug (represented by formula B):

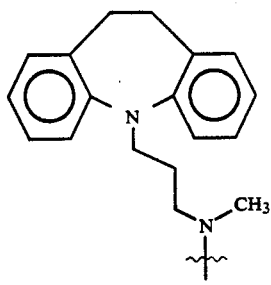

A

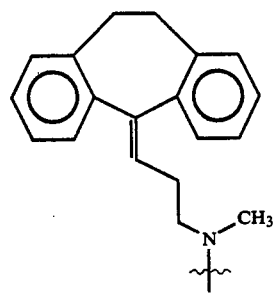

B

Preferably, one or both, preferably both, the drug compounds are bound to the carrier protein by means of bridging groups.

The bridging groups may be the same or different for each drug compound. Preferably, the bridging groups are selected from $C_2$ to $C_6$ alkyl carbonyl or $C_2$ to $C_6$ alkyl dicarbonyl groups. More preferably, the bridging groups are selected from $C_2$ to $C_6$ alkyl carbonyl groups. More preferably, the bridging groups are selected from ethylcarbonyl, propylcarbonyl or butylcarbonyl groups. Preferably, the bridging groups are ethylcarbonyl groups.

Preferably, the carrier protein is keyhole limpet haemacyanin.

Preferably, the immunogen comprises (Desipramine ethylcarbonyl)-KLH-(nortriptyline ethylcarbonyl) [D-N mix].

According to a second aspect of the present invention there is provided a method of raising antisera to a drug wherein an immunogenic composition according to the first aspect of the present invention is used to immunise an animal.

The animal may be a large or small animal, for example a mouse, rat, sheep, goat, donkey or horse. Preferably, the animal is a sheep. More preferably, the animal is a Welsh half-bred sheep.

According to the third aspect of the present invention there is provided a process for the preparation of a pharmaceutical composition comprising mixing antisera raised to an immunogen according to the first aspect of the present invention with a pharmaceutically acceptable excipient.

According to the fourth aspect of the present invention there is provided a method of alleviating an overdose of a tricyclic antidepressant drug comprising administering to a patient suffering from such an overdose an effective amount of antisera raised to an immunogen according to the first aspect of the present invention.

The antisera produced may be used in their natural polyclonal form or may be used in a modified form. Preferably, the antisera are modified by isolation of the Fab fragments of the whole antibodies (IgG). This may be accomplished by the standard techniques of papain digestion of the whole antisera followed by purification of the Fab fragments by affinity chromatography. Alternatively, cells from the immunized animal, e.g. spleen cells, may be isolated for the production of monoclonal antibodies by standard procedures.

The invention will now be described by way of example. It will be understood, however, that the invention is described by way of example only and modifications of details may be made within the scope of the invention.

EXAMPLE 1

Drug Derivatives

The following drug derivatives were prepared and used for the preparation of immunogens.

1.1 Desipramine free base

Structure:

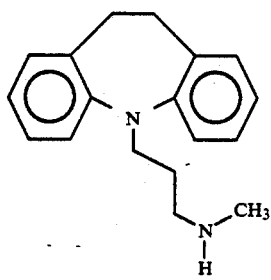

Preparation: 2 g desipramine hydrochloride (Sigma) was dissolved in 500 ml distilled water. Solid sodium carbonate (BDH) was then added in small amounts with stirring. The addition was continued until a white fine precipitate persisted. The aqueous suspension was extracted with 3×500 ml chloroform (BDH). The chloroform layers were combined and dried with solid magnesium chloride (BDH GPR). The inorganic material was removed by filtration and the chloroform removed by rotary evaporation to give a pale amber coloured oil. Yield 1.4–1.7 g. This product gave only one spot by TLC (see below 3.1) eluting with methanol.

1.2 Desipramine ethyl carbonyl acid (DEC)

Structure:

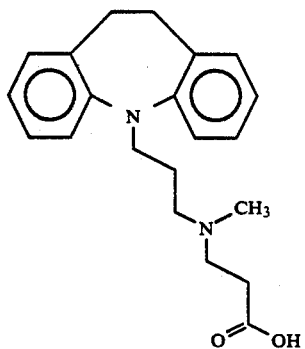

Preparation: 1.3 g desipramine free base (1.1), and 0.38 g methyl acrylate were dissolved in 40 ml methanol (BDH Analar). The mixture was stirred and refluxed for 70 hours under a nitrogen atmosphere. TLC showed one product (Rf 35 0.45 methanol solvent; see 3.1) with a small amount of desipramine starting material still present. The mixture was reduced in volume to viscous oil. The oil was dissolved in 6 ml 1.0M hydrochloric acid and then 100 ml water was added. 15 ml 1.0M sodium hydroxide was added to the solution giving a white precipitate. This suspension was refluxed for 4 hours by which time the precipitate had disappeared. The solution was cooled to room temperature and extracted with 2×100 ml ether (Rathburn GDR) to remove any unreacted desipramine from the aqueous phase. The pH of the aqueous layers was adjusted to 7.5 by addition of 1.0M hydrochloric acid giving a fine white precipitate. The solution was cooled to 4° C. for 2 hours and the precipitate recovered by filtration, washed with 40 ml distilled water and dessicated over silica under vacuum for 3 days. Yield 0.865 g (52%). The product gave one spot (Rf 0.45 methanol solvent see 3.1) with a very faint spot at 0.2 corresponding to desipramine.

1.3 Desipramine valeric acid (DVA)

Structure:

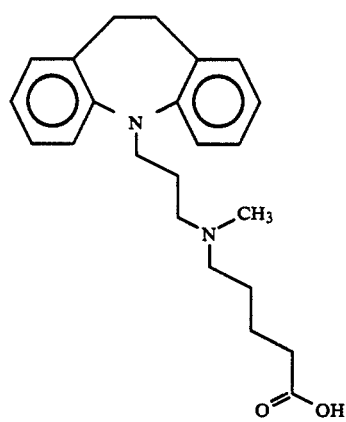

Preparation: 1.605 g desipramine free base (1.1) 0.506 g sodium bicarbonate (BDH Analar) and 1.175 g methylbromovalerate were mixed in 2 ml dry DMF (Aldrich sureseal). The mixture was stirred under a nitrogen atmosphere and maintained at a temperature of 120° C. for 4 hours. TLC showed the complete disappearance of the starting material and the formation of a single product (methanol as eluent on plates described below). 50 ml distilled water was added to the cooled solution and the aqueous suspension was extracted with 3×50 ml of chloroform. The chloroform layers were combined, dried with magnesium chloride (as in 1.1) and the chloroform removed by rotary evaporation. The resulting brown liquid was vacuum distilled to remove a colourless oil (bp 60° C. at −1.0 bar). The residual brown viscous liquid gave one major spot, Rf 0.8, by TLC (CH$_2$Cl$_2$:MeOH, 3:2 see 3.1) with a very slight desipramine impurity.

The structure of this product is thought to be:

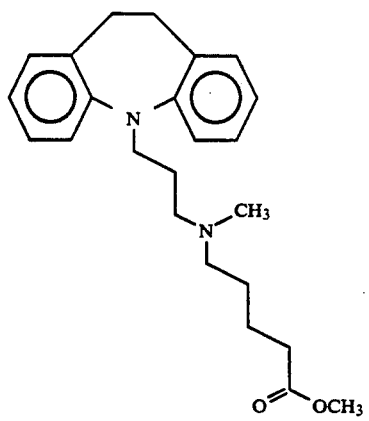

The brown viscous oil was then suspended in 20 ml of 0.05 g/ml aqueous sodium hydroxide solution. The mixture was refluxed for 4 hours with stirring. TLC showed that the starting material had disappeared and that a new product had formed, Rf 0.2 (CH$_2$Cl$_2$:MeOH 3:2 eluent see 3.1). The cooled solution was extracted with 3×40 ml ether (Rathburn GDR) and the aqueous layer retained (this removed a slight desipramine impurity). Careful dropwise addition of concentrated hydrochloric acid (BDH Analar) gave a white precipitate at pH 6.0. This suspension was extracted with 3×50 ml dichloromethane. The dichloromethane layers were combined, dried with magnesium chloride (see 1.1) and the solvent removed by rotary exporation. The product was a dark brown oil that gave one spot by TLC, Rf 0.2 (CH$_2$Cl$_2$:MeOH 3:2 eluent 3.1).

1.4 Nortriptyline free base

Structure:

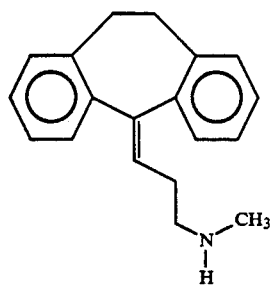

Preparation: 2 g nortriptyline hydrochloride (Sigma) was dissolved in 500 ml distilled water. Solid sodium carbonate (BDH) was then added in small amounts with stirring. The addition was continued until a white fine precipitate persisted. The aqueous suspension was extracted with 3×500 ml chloroform (BDH). The chloroform layers were combined and dried with solid magnesium chloride (BDH GPR). The inorganic material was removed by filtration and the chloroform removed by rotary evaporation to give a pale amber coloured oil. Yield 1.4–1.7 g. This product gave only one spot by TLC (see below 3.1) eluting with methanol.

1.5 Nortriptyline ethyl carboxylic acid (NEC)

Structure:

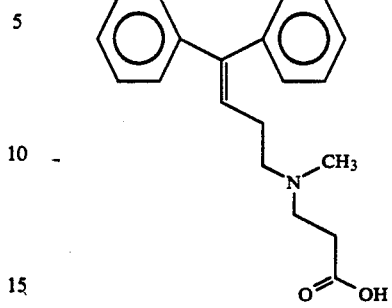

Preparation: 1.6 g nortriptyline free base (1.4) and 0.625 g methyl acrylate were dissolved in 50 ml methanol (BDH Analar). The mixture was stirred and refluxed for 48 hours under a nitrogen atmosphere. TLC showed one product (Rf 0.70 methanol solvent; see 3.1) with a small amount of nortriptyline starting material still present. The mixture was reduced in volume to a viscous oil. The oil was dissolved in 10 ml 1.0M hydrochloric acid and then 50 ml water was added. 5 ml 5.0M sodium hydroxide was added to the solution giving a white precipitate. This suspension was refluxed for 4 hours by which time the precipitate had disappeared. The solution was cooled to room temperature and extracted with 3×50 ml ether (Rathburn GDR) to remove any unreacted nortriptyline from the aqueous phase. The pH of the aqueous layer was adjusted to 7.5 by addition of 1.0M hydrochloric acid giving a fine white precipitate. The solution was cooled to 4° C. for 24 hours and the precipitate recovered by filtration, washed with 40 ml distilled water and dessicated over silica under vacuum for 3 days. Yield 0.600 g (30%). The product gave one spot (Rf 0.70 methanol solvent see 3.1).

1.6 Fluorescein thiocarbamyl ethylenediamine (FTC-ED)

Structure:

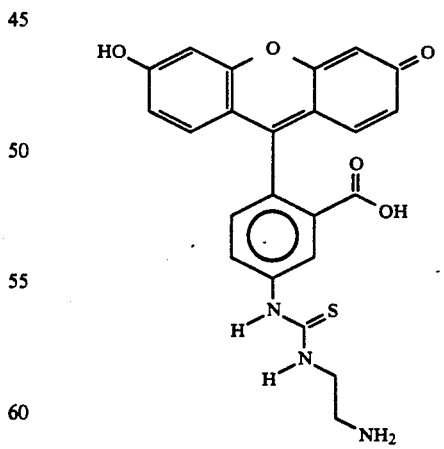

Ethylenediamine dihydrochloride (220 mg, 1.5 mmol) was dissolved in 50 ml of methanol containing 10 ml/l triethylamine. FITC (130 mg Aldrich isomer 1) was dissolved in 10 ml of the same solvent and added dropwise to the ethylenediamine solution over 1 hr. The mixture was left stirring overnight at 4° C. in the dark.

The orange precipitate formed was then filtered, washed with 200 ml of methanol and then dried (over silica under vacuum) to yield 120 mg of product which was used without further purification. A small sample of the product was run on Whatman No. 3 MM paper (0.05M sodium bicarbonate as eluent) and gave one spot at Rf. 0.4.

1.7 Desipramine valeroyl fluorescein ethylenediamine

Structure:

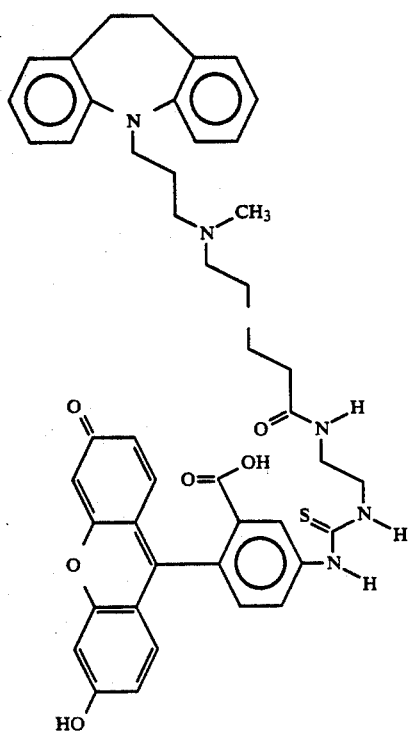

20 mg desipramine valeric acid (1.3), 21 mg EDC and 12 mg N-hydroxysuccinimide were dissolved and stirred in 0.8 ml acetonitrile and one drop of water. After 40 mins the reaction was analysed by TLC (3.1, dichloromethanie:methanol 3:2 eluent) showing that the active ester had completely formed. 24 mg FTC-ED (1.6) dissolved in 1 ml DMF (Aldrich sureseal) +6 drops of water was then added dropwise over 40 mins in 100 μl aliquots to the stirring active ester solution. After 2 hrs (or when complete by analytical TLC) the solution was loaded onto two preparative TLC plates (Merck 5715 eluent as above). The single bright green/red band (Rf 0.4) was removed and eluted with methanol. The silica was removed by centrifugation and the superantant stored at −20° C. in the dark. 1 ml of the solution was diluted with pH 9.0 carbonate (3.2) and the concentration of the tracer assessed by the method of Sidki AM, Al-Abdulla IH and Rowell FJ (Sidki et al. Clin.Chem. (1987) 33:463-67].

EXAMPLE 2

Immunogens 2.1 (Desipramine ethylcarbonyl)-KLH-(nortriptyline ethylcarbonyl) [D-Nmix]

Structure:

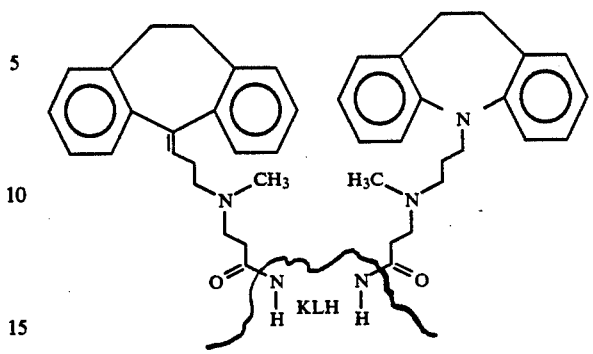

Preparation: 100 mg NEC (1.5), 120 mg EDC and 70 mg NHS were dissolved in 1.5 ml DMF (Aldrich sureseal) and 2 drops of water. The mixture was stirred for 60 mins at room temperature and then 120 mg of EDC was added. The reaction was followed by TLC (MeOH as eluent, see 3.1) and showed one spot after 90 mins, Rf. 0.8. Starting material, by contrast, gave a spot at Rf 0.2. Coincident with the above procedure 100 mg DEC (1.2), 57 mg EDC and 34 mg NHS were dissolved in 1.0 ml DMF (Aldrich sureseal) and 2 drops of water. The mixture was stirred at room temperature for 1 hr. and then 57 mg of EDC was added. The reaction was followed by TLC (MeOH as eluent see 3.1) and showed only one spot after 90 mins, Rf 0.8. Starting material, by contrast, gave a spot at Rf about 0.2. This solution was then mixed with the NEC active ester solution (described above) and stirred for 5 mins. The mixture was added dropwise to a stirred solution of 200 mg KLH (Calbiochem) in 40 ml pH 9.0 carbonate buffer (see below for composition). 75 mg amounts of EDC were added to the stirring solution as follows:

| Day 1 | Addition of active ester solns. no extra EDC. |
| --- | --- |
| Day 2 | 75 mg |
| Day 3 | 75 mg adjusted pH 7.5 to 8.5 with Na$_2$CO$_3$. |
| Day 4 | 75 mg |
| Day 5 | continued stirring: no more EDC added. |

The suspension was left at 4° C. for 3 days and then was extensively dialysed for 3 days. The contents of the dialysis bag were then freeze dried for 3 days and stored at −20° C. The solid was weighed out for immunisation as described in section 4.1–4.2 below.

2.2 Desipramine ethylcarbonyl-KLH (DECD-KLH)

[Comparative Example]

Structure:

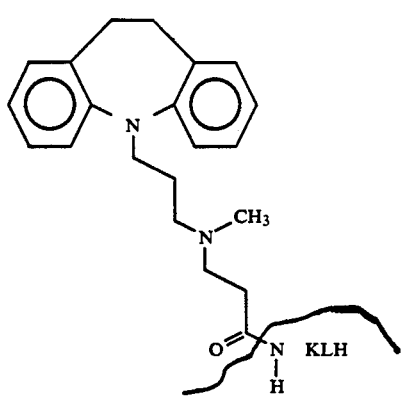

Preparation: 100 mg DEC (see section 1.2), 34 mg NHS (Sigma) and 57 mg EDC (Sigma) were dissolved in 2 ml DMF (Aldrich sureseal) and two drops of water (distilled). The structure of the "active ester" formed is as follows:

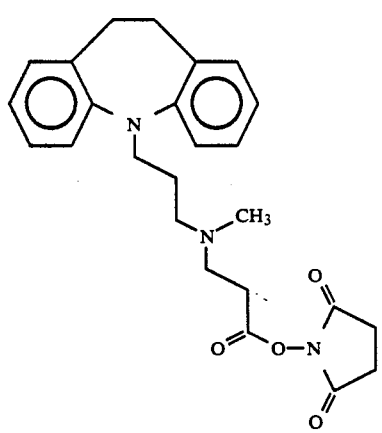

The mixture was stirred and the reaction monitored by TLC (see below for details of the plates (3.1) using methanol as the eluent. After 2 hours the reaction mixture gave two spots on the TLC plate of similar intensity (Rf 0.2 and 0.5). This solution was added dropwise to a stirred solution of 100 mg KLH (calbiochem) in 20 ml pH 9.0 carbonate buffer (see below for composition). 50 mg EDC (Sigma) was added after 36 hours and the solution stirred for a further 6 hours. The resulting white suspension was extensively dialysed against tap water for 3 days. The contents of the dialysis bag were then freeze dried for 3 days and stored at −20° C. This solid was then weighted in the manner described below for immunisation 4.1–4.2.

2.3 Nortriptyline ethylcarbonyl-KLH (NEC-KLH) [Comparative Example]

Structure:

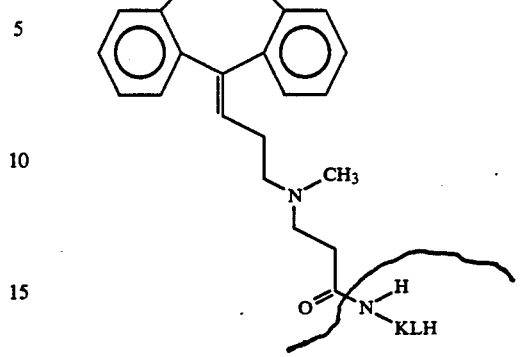

Preparation: 100 mg NEC (see section 1.5), 70 mg NHS (Sigma) and 120 mg EDC (Sigma) were dissolved in 1 ml DMF (Aldrich sureseal) and two drops of water (distilled). The structure of the "active ester" formed is as follows:

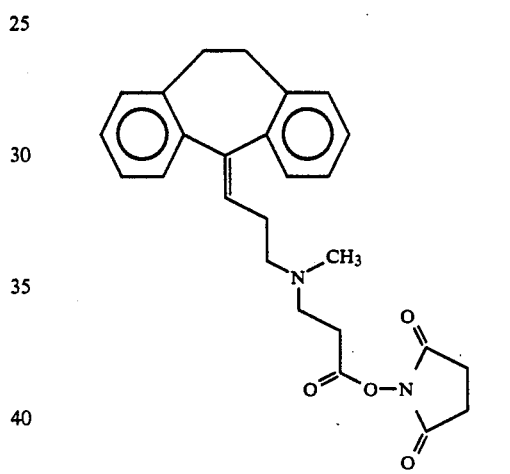

The mixture was stirred and the reaction monitored by TLC (for details of the plates see 3.1) using methanol as the eluent. After 60 mins the reaction mixture gave two spots on the TLC plate (Rf 0.2 and 0.7). The spot at 0.7 (starting material) was of similar intensity to the other. 120 mg EDC was added to the mixture, 30 minutes later and the TLC showed only the spot at Rf 0.7. This solution was added dropwise to a stirred solution of 200 mg KLH (calbiochem) in 40 ml pH 9.0 carbonate buffer (see below for composition).

| | |
|---|---|
| Day 1 | details above |
| Day 2 | 75 mg EDC added |
| Day 3 | pH adjusted to 8.5 with Na$_2$CO$_3$ + added 75 mg EDC |
| Day 4 | 75 mg EDC added |
| Day 5 | left at 4° C. for three days. |

The resulting white suspension was extensively dialysed against tap water for 3 days. The contents of the dialysis bag were then freeze dried for 3 days and stored at −20° C. This solid was then weighed in the manner described for immunisation (4.1–4.2).

2.4 (Desipramineethylcarbonyl)-KLH-(Desipramine butylcarbonyl) "DMix" Structure:

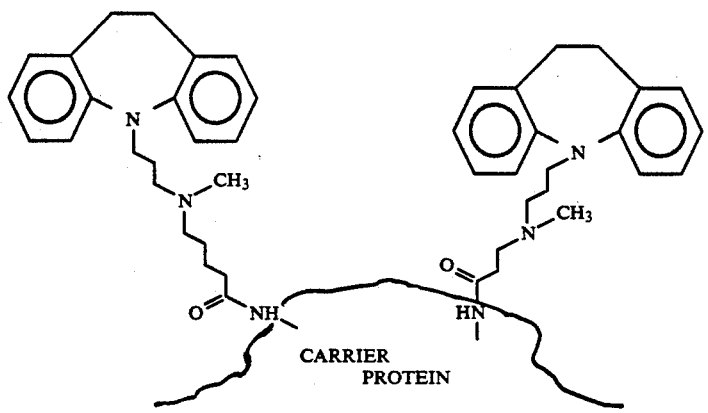

Preparation: 75 mg DVA (1.3), 78 mg EDC and 48 mg NHS were dissolved in 1.5 ml DMF (Aldrich sureseal) and 2 drops of water. The mixture was stirred for 15 minutes at room temperature and then 40 mg of EDC was added. After an hour of stirring another 40 mg quantity of EDC was added to the mixture. The reaction was followed by TLC (MeOH as eluent, see 3.1) and showed one spot only after 90 mins. Rf at 0.6. Starting material, by contract, gave a spot at Rf 0.2. The structure of the active ester was as in 2.7.

One hour before the above procedure was begun 75 mg DEC (1.2), 86 mg EDC and 51 mg NHS were dissolved in 1.5 ml DMF (Aldrich sureseal) and 2 drops of water. The mixture was stirred at room temperature 1 hr. and then 43 mg of EDC was added. The reaction was followed by TLC (MeOH as eluent see 3.1) and showed only one spot after 150 mins, Rf 0.5. Starting material, by contrast, gave a spot at Rf about 0.2. The structure of the active ester solution was as in 2.6. This solution was then mixed with the DVA active ester solution (described above) and stirred for 5 mins. TLC (MeOH eluent see 3.1 etc.) of this mixture showed two spots, overlapped at RF about 0.5. The mixture was added dropwise to a stirred solution of 100 mg KLH (Calbiochem) in 20 ml pH 9.0 carbonate buffer (see below for composition). 50 mg amounts of EDC were added to the stirring solution as follows:

| Day 1 | 50 mg 4 hrs after active ester addition |
| --- | --- |
| Day 2 | 50 mg |
| Day 3 | 50 mg |
| Day 4 | 50 mg |
| Day 5 | 50 mg |

The suspension was left at 4° C. for 3 days and then was extensively dialysed for 3 days. The contents of the dialysis bag were then freeze dried for 3 days and stored at −20° C. The solid was weighed out for immunization as described in section 4.1–4.2 below.

2.5 Two Immunogens individually made Mixed Together: "Dcomb"

Desipramine ethylcarbonyl-KLH (2.6) mixed with Desipramine butylcarbonyl-KLH (2.7).
Structure:

Preparation: 20 mg DVA-KLH (2.2) and 20 mg DEC-KLH (2.1) were thoroughly mixed together. The resulting solid material was weighted out for immunization as described in section 4.1–4.2 below.

2.6. Desipramine ethylcarbonyl-KLH (DEC2-KLH) [Comparative Example]

Structure:

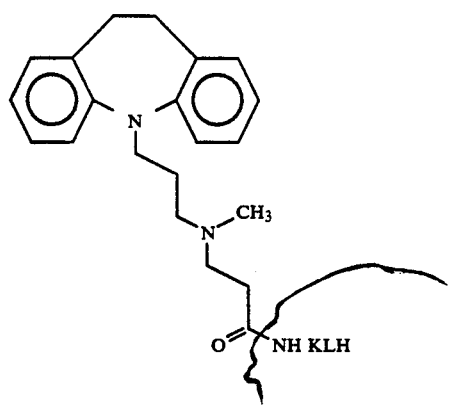

Preparation: 100 mg DEC (see section 1.2), 34 mg NHS (Sigma) and 57 mg EDC (Sigma) were dissolved in 2 ml DMF (Aldrich sureseal) and two drops of water (distilled). The structure of the "active ester" formed is as follows:

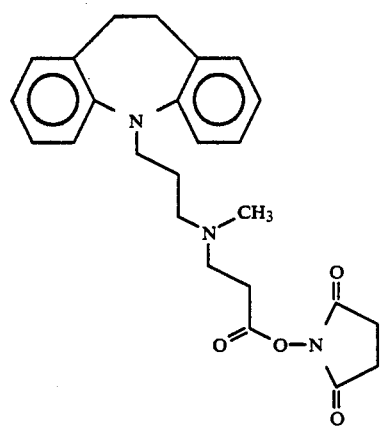

The mixture was stirred and the reaction monitored by TLC (see below for details of the plates 3.1) using methanol as the eluent. After 10 mins the reaction mixture gave two spots on the TLC plate (Rf 0.2 and 0.5). The spot at 0.2 (starting material) was more intense than the other. After 30 mins 57 mg EDC and 34 mg NHS were added to the mixture, 20 mins later a further 57 mg EDC was added and the TLC showed that a spot at Rf 0.5 was much stronger. This solution was added dropwise to a stirred solution of 100 mg KLH (Calbiochem) is 20 ml pH 9.0 carbonate buffer (see below for composition). 50 mg amounts of EDC were added to the stirring solution as follows:

| Day 1 | 50 mg 4 hrs after active ester addition. |
|---|---|
| Day 2 | 50 mg |
| Day 3 | 50 mg |
| Day 5 | 50 mg dialysis started 4 hrs later. |

The resulting white suspension was extensively dialysed against tap water for 3 days. The contents of the dialysis bag were then freeze dried for 3 days and stored at −20° C.

2.7 Desipramine butylcarbonyl-KLH (DVA-KLH) [Comparative Example]

Structure:

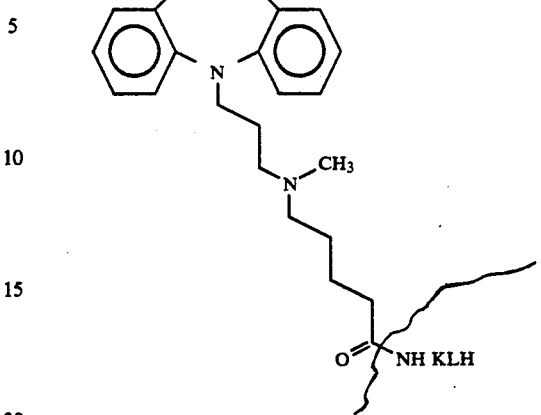

Preparation: 100 mg DVA (see section 1.3), 63 mg NHS (Sigma) and 105 mg EDC (Sigma) were dissolved in 2 ml acetonitrile (BDH) and two drops of water (distilled). The structure of the "active ester" formed is as follows:

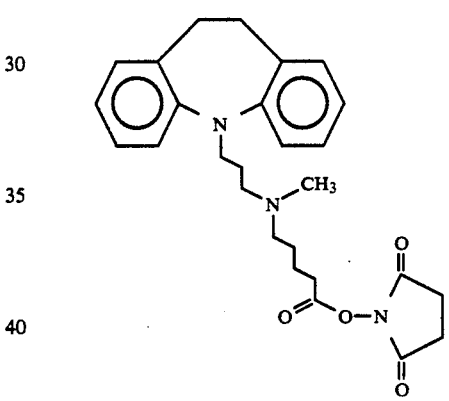

The mixture was stirred and the reaction monitored by TLC (see below for details of the plates 3.1) using methanol as the eluent. After 10 mins the reaction mixture gave two spots on the TLC plate (Rf 0.2 and 0.6). After 80 mins the spot at Rf 0.6 was the only one visible i.e. all the starting material had disappeared. This solution was added dropwise to a stirred solution of 100 mg KLH (Calbiochem) in 20 ml pH 9.0 carbonate buffer (see below for composition). 50 mg amounts of EDC were added to the stirring solution as follows:

| Day 2 | 50 mg |
|---|---|
| Day 3 | 50 mg |
| Day 4 | 50 mg |
| Day 5 | 50 mg |
| Day 8 | Dialysis |

The resulting white suspension was extensively dialysed against tap water for 2 days. The contents of the dialysis bag were then freeze dried for 3 days and stored at −20° C.

EXAMPLE 3

Systems and Abbreviations

3.1 Thin Layer Chromatography Systems

Many of the above protocols involved the use of TLC plates. All the work was done using aluminium backed silica plates ($60F_{254}$ Merch Art. 5554). The plates were run in a small developing tank or jar with the solvent system specified.

3.2 Buffers and Abbreviations pH 9.0 carbonate buffer = 1.59 g sodium carbonate + 2.93 g sodium bicarbonate dissolved in 1000 ml distilled water. pH adjusted to 9.0 with aqueous sodium hydroxide. All reagents BDH AnalaR.

PBS = phosphate buffered saline = sodium chloride 8.0 g + potassium chloride 0.2 g + disodium hydrogen orthophosphate 1.15 g + potassium dihydrogen orthophosphate 0.2 g. All reagents were BDH AnalaR, dissolved in 1000 ml distilled water.

KLH = Keyhole limpet haemacyanin (Calbiochem 374817).

EDC 1-Ethyl-3-(3-dimethylaminopropyl)-carbodiimide (Sigma E 6383).

DMF = Dimethylformamide (BDH AnalaR).

NHS N-hydroxysuccinimide (Sigma H7377).

TLC = thin layer chromatography (see 3.2).

EXAMPLE 4

Immunization

The following protocol for immunization of Welsh half-bred sheep was carried out for all the above immunogens.

4.1 The primary immunisation: 12 mg lyophilized immunogen was suspended in 0.5 ml ethanol and 3.5 ml PBS. 10 ml Freunds complete ajuvant was added and the vial shaken to produce an emulsion. This was injected by the sub-cutaneous route into 3 sheep.

4.2 Reimmunizations: 6 mg lyophilized immunogen was suspended in 0.5 ml ethanol and 3.5 ml PBS. 10 ml Freunds incomplete adjuvant was added and the vial shaken to produce an emulsion. This was injected by the sub-cutaneous route into 3 sheep.

After the primary immunization was given, the reimmunizations were made every 4 weeks thereafter. Samples were taken of the sheep serum two weeks after each reimmunisation (starting after the second reimmunization). Table II summarises the protocol:

TABLE II

| week | action |
|---|---|
| 0 | primary immunization |
| 4 | reimmunization |
| 8 | reimmunization |
| 10 | sample |
| 12 | reimmunization |
| 14 | sample |
| 16 | reimmunization |
| 18 | sample |
| 20 | reimmunization |
| etc | etc |

EXAMPLE 5

Assessment of Antisera

The antisera raised to each of the immunogens in Section 2 above were assessed by Enhancement fluoroimmunoassay (EFIA). The method depends on the fluorescein-drug tracer (1.7) giving a stronger fluorescent emission when bound to antibody than when free in solution.

This phenomenon has been observed in, for example, a thyroxine-fluorescein conjugate [Smith D. S. FEBS Letts. (1977) 77:25-27]. It is believed that the tricyclic ring system acts as a quenching group to the excited fluorescein when the molecule is free in solution. On binding to antibody the ring system is unable to interact with the excited state of the fluorescein and so the fluorescent signal is unquenched.

5.1. Assessment of Specific Antibody Concentrations

To doubling dilutions of 1 ml of antisera 0.5 ml of 30 nM tracer was added (giving a final assay concentration of 10 nM).

The assay diluent buffer and tracer buffer was PBS (see 3.2) containing 0.05% bovine gamma globulin.

After 60 mins incubation in the dark the samples were read using a Perkin-Elmer LS20 polarization fluorimeter ($\lambda_{ex}$492, $\lambda_{em}$517 nm).

A control solution with 1 ml of assay + 0.5 ml tracer solution was also prepared. A dilution curve was obtained by plotting the fluorescence intensity against the final dilution of the antisera. A typical dilution curve is shown in FIG. 1.

To calculate the "50% dilution" the following equation was used.

$$\left( \frac{\text{PLATEAU VALUE} - \text{CONTROL VALUE}}{2} \right) + \text{CONTROL VALUE}$$

From this value the corresponding dilution was read from the curve.

The g/l of antibody (specific) may then be calculated.

Total tracer concentration 10 nM. At 50%, 5 nM tracer is bound therefore 5 nM binding sites are present at that dilution.

Therefore 2.5 nM antibody is present (2 sites/IgG). Hence the g/l is calculated:

"50% dilution" × 2.5 nM × 160,000 (M.W. IgG)

The use of the particular tracer (a desipramine/imipramine derivative) to assess antisera to nortriptyline/amitriptyline immunogens may lead to an underestimate of titre of these immunogens. However, the cross-reactivity studies below (5.2) show that the tracer is easily displaced by all the members of the TCA family tested and so is an appropriate tracer for this work. It is the experience of the inventor that the present assay system provided a good method of assessing the titre of the immunogens or the present invention.

5.2. Cross-reactivity Studies

A principal objection of this work has been to achieve high titre antisera with a broad cross-reactivity to the TCA's. The four most important TCA's (imipramine, desipramine, amitriptyline and nortriptyline) were assessed as to their ability to displace the tracer from a constant concentration of antibody.

The dilution corresponding to 80% of the plateau value read from the curve in 5.1 was taken for each of the 10 week antisera pools.

TCA (imipramine, desipramine, amitriptyline or nortriptyline) was added to the antisera to give final assay concentrations as follows:

1.67, 3.33, 6.67, 13.33, 66.67 nM

Fluorescein labelled desipramine tracer (1.7) was added so as to give a 10 nM final concentration. A typical essay was performed as follows:

| | |
|---|---|
| 900 ʌ ml | antibody to give a final assay concentration corresponding to 80% the plateau value. |
| +100 ʌ ml | drug to give a final concentration as listed above. |
| +500 ʌ ml | 30 nM tracer (final concentration 10 nM) |

The tubes were mixed and incubated in the dark for one hour and the fluorescence intensity measured.

Figure 2:
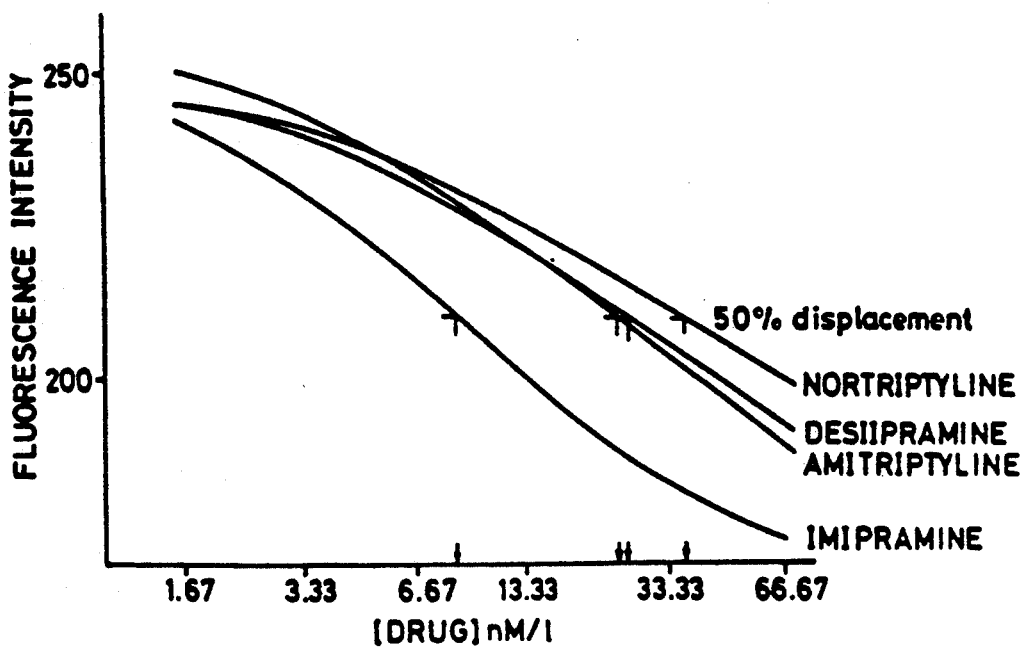
FIG. 2 illustrates a set of dilution curves obtained by plotting fluorescence intensity against drug concentration in a cross-reactivity study based on an enhancement fluoroimmunoassay.

A typical set of standard curves is shown in FIG. 2.

The 50% displacement point of each label was taken and the concentration of each drug compared. The desipramine hydrochloride 50% concentration was called 100% displacement value and the other drugs compared.

$$\% \text{ cross-reactivity} = \frac{\text{Desipramine 50\% displacement concn.}}{\text{Drug 50\% displacement concn.}} \times 100$$

The Nortriptyline hydrochloride 50% value was called 100% when assessing NEC-KLH.

Figure 3:
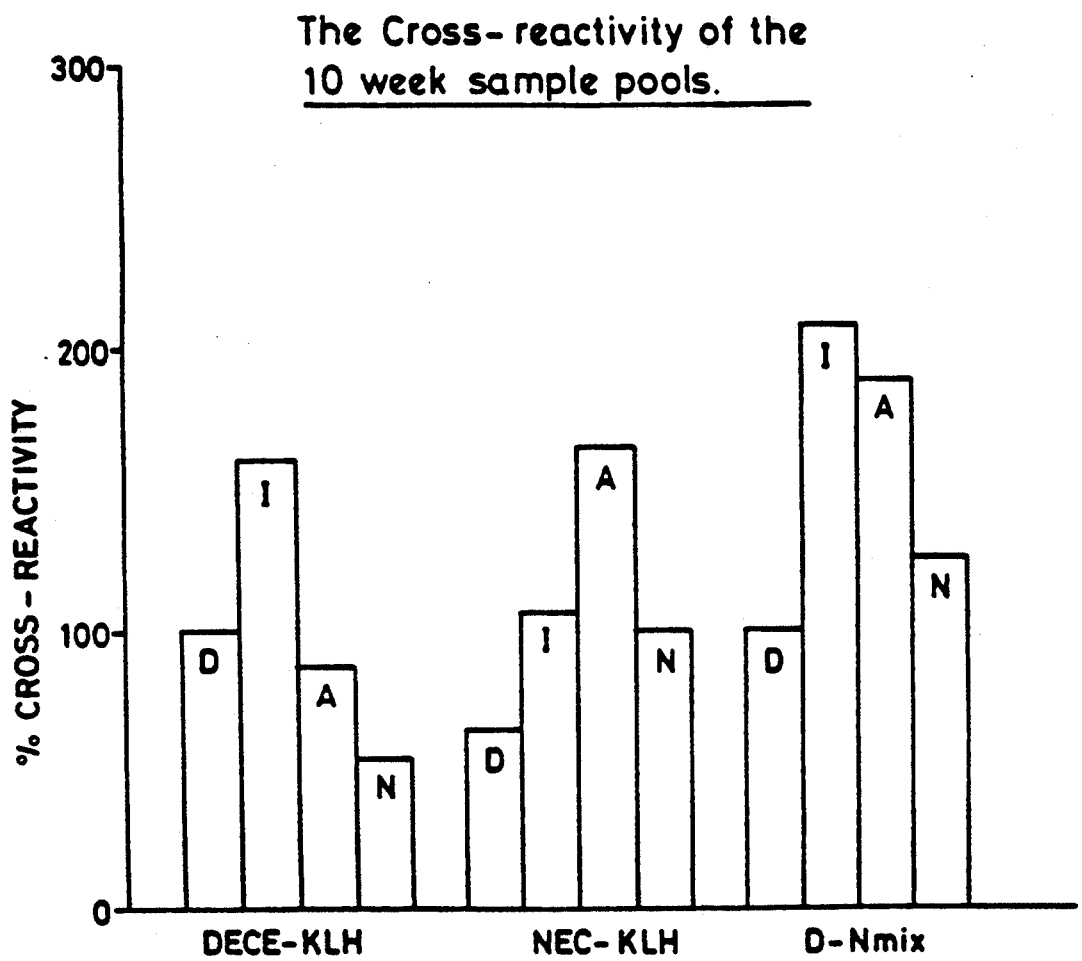
FIG. 3 illustrates the relative cross-reactivities, to various TCA-drugs, of antisera raised to an immunogenic composition according to the present invention in comparison to antisera raised to conventional immunogens.

The results are tabulated in Table III and FIG. 3:

TABLE III

| IMMUNOGEN | DECE-KLH | NEC-KLH | D-Nmix |
|---|---|---|---|
| CONCN EFIA g/l | 4.1 | 4.0 | 5.2 |
| % cross reactivity | | | |
| Desipramine | 100 | 64 | 100 |
| Imipramine | 160 | 106 | 208 |
| Amitriptyline | 87 | 164 | 188 |
| Notriptyline | 54 | 100 | 125 |

The results demonstrate that the immunogens of the present invention may be used to raise antisera in higher titre and with broader cross-reactivity properties than conventional immunogens.

What is claimed is:

1. An immunogenic composition for raising a cross-reactive antisera to tricyclic antidepressant drugs, wherein said composition comprises an immunogen, said immunogen comprising an immunologically active carrier protein to which is bound at least two types of hapten, each hapten comprising a drug molecule, wherein the drug molecule of one type of hapten is chosen from the desipramine/imipramine series of tricyclic antidepressant drugs and the drug molecule of a second type of hapten is chosen from the nortriptyline/amitriptyline series of tricyclic antidepressant drugs.

2. The immunogenic composition according to claim 1 wherein each hapten further comprises a bridging group.

3. The immunogenic composition according to claim 1 wherein the carrier protein is keyhole limpet haemacyanin.

4. The immunogenic composition according to claim 2, wherein said bridging group is chosen from the group consisting of an organic molecule, an amino acid, a peptide, a protein, a saccharide, a polysaccharide, a carbohydrate, a polyamino acid, and a synthetic polymer.

5. The immunogenic composition according to claim 1, wherein the drug molecule of each hapten is chosen from the group consisting of Amitriptyline, Butriptyline, Clomipramine, Desipramine, Dibenzepine, Dothiepin, Doxepin, Imipramine, Iprindole, Maprotiline, Mianserin, Nomifensine, Nortriptyline, Opipramol, Protriptyline, Trimipramine, and Zimelidine.

6. The immunogenic composition according to claim 1, wherein the immunogen comprises (Desipramine ethylcarbonyl)-KLH-(nortriptyline ethylcarbonyl).

7. The immunogenic composition according to claim 1 wherein the immunogen is chosen from the group consisting of desipramine ethylcarbonyl-KLH-nortriptyline ethylcarbonyl and desipramine ethylcarbonyl-KLH-desipramine butylcarbonyl.

8. The immunogenic composition according to claim 1, wherein the drug molecule for both haptene is chosen from the desipramine series of drugs.

9. The immunogenic composition according to claim 8, wherein the drug molecules are desipramine-ethylcarbonyl and desipramine butylcarbonyl.

10. A process for the preparation of a modified antisera to a drug, wherein said process comprises:
1) immunizing an animal with an immunogenic composition according to claim 1;
2) obtaining antisera from said animal; and
3) modifying the antisera and isolation the Fab fragments of the whole antibodies.

11. A method of raising antisera to a drug, said method comprising immunizing an animal with an immunogenic composition according to claim 1.

12. A process for the preparation of a pharmaceutical composition, said process comprising mixing antisera raised to an immunogen according to claim 1 with a pharmaceutically acceptable excipient.

13. A pharmaceutical composition comprising an antisera raised to an immunogenic composition according to claim 1 together with a pharmaceutically acceptable excipient, wherein said antisera is provided in an amount effective to treat an overdose of a tricyclic antidepressant drug.

14. A pharmaceutical composition according to claim 13 wherein the antisera is a modified antisera comprising Fab fragments.

15. A method of alleviating an overdose of a tricyclic antidepressant drug, said method comprising administering to a patient suffering from such an overdose an amount of the pharmaceutical composition according to claim 13 effective to treat said overdose.

16. A method of alleviating an overdose of a tricyclic antidepressant drug, said method comprising administering to a patient suffering from such an overdose an amount of the antisera raised to an immunogenic composition according to claim 1 effective to treat said overdose.

17. A method of raising antisera to a drug, wherein the titre of said antisera is greater than 4.0 g/l, said method comprising immunizing an animal with an immunogenic composition according to claim 1.

18. A method of raising antisera to a drug, wherein the titre of said antisera is greater than 5.0 g/l, said method comprising immunizing an animal with an immunogenic composition according to claim 1.

* * * * *

UNITED STATES PATENT AND TRADEMARK OFFICE
CERTIFICATE OF CORRECTION

PATENT NO. : 5,256,409
DATED : October 26, 1993
INVENTOR(S) : Stuart J.F.E. Blincko It is certified that error appears in the above-indentified patent and that said Letters Patent is hereby corrected as shown below:

Column 24, line 31, deleye "isolation" and substitute therefor
--isolating--.

Signed and Sealed this

Tenth Day of May, 1994

Attest:

BRUCE LEHMAN

*Attesting Officer*   *Commissioner of Patents and Trademarks*